(12) United States Patent
Albrecht et al.

(10) Patent No.: US 9,040,079 B2
(45) Date of Patent: *May 26, 2015

(54) PEGYLATED COMPOUNDS FOR AGE-RELATED MACULAR DEGENERATION

(75) Inventors: Volker Albrecht, Bergholz-Rehbrücke (DE); Stefan Spaniol, Bonn (DE); Dietrich Scheglmann, Jena (DE)

(73) Assignee: Biolitec Pharma Marketing Ltd, Labuan (MY)

( * ) Notice: Subject to any disclaimer, the term of this patent is extended or adjusted under 35 U.S.C. 154(b) by 705 days.

This patent is subject to a terminal disclaimer.

(21) Appl. No.: 12/743,489

(22) PCT Filed: Nov. 19, 2008

(86) PCT No.: PCT/US2008/012905
§ 371 (c)(1),
(2), (4) Date: May 18, 2010

(87) PCT Pub. No.: WO2009/067203
PCT Pub. Date: May 28, 2009

(65) Prior Publication Data
US 2010/0247626 A1     Sep. 30, 2010

Related U.S. Application Data

(60) Provisional application No. 61/003,653, filed on Nov. 19, 2007.

(51) Int. Cl.
*A61K 9/127* (2006.01)
*A61K 49/00* (2006.01)
(Continued)

(52) U.S. Cl.
CPC ........... *A61K 49/0084* (2013.01); *A61K 9/0051* (2013.01); *A61K 9/1271* (2013.01); *A61K 41/0071* (2013.01); *A61K 47/48215* (2013.01)

(58) Field of Classification Search
CPC ...................................................... A61K 9/127
USPC ............................................................ 424/450
See application file for complete search history.

(56) References Cited

U.S. PATENT DOCUMENTS 5,190,761 A * 3/1993 Liburdy ..................... 424/450
5,389,378 A * 2/1995 Madden ..................... 424/450
(Continued)

FOREIGN PATENT DOCUMENTS

GB            2 146 525    *  4/1985

*Primary Examiner* — Gollamudi Kishore
(74) *Attorney, Agent, or Firm* — Bolesh J. Skutnik; B J Associates

(57) ABSTRACT

A special photosensitizer formulation and Photodynamic Therapy method for treating choroidal neovascularization (CNV) associated with age-related macular degeneration (AMD) is provided. CNV is a major cause for vision loss in elderly patients. A special drug delivery formulation is used to encapsulate the hydrophobic photosensitizer, preferably a pegylated liposome. This improves the solubility and therapeutic index of the photosensitizers. In one preferred embodiment, a pegylated photoactive agent remains confined in the intravascular compartment of neovasculature for a longer duration. Thus efficient elimination of neovascular proliferation and minimal damage to extravascular tissue and normal vessels is ensured. In this method, a hydrophobic photosensitizer, that is able to photochemically destroy neovessels, is injected into the patient. CNV irradiation with a non-thermal laser follows after a predefined time interval. The excited photosensitizer photocoagulates newly formed blood vessels thereby improving the vision and preventing further loss of vision.

5 Claims, 3 Drawing Sheets

(51) Int. Cl.
*A61K 9/00* (2006.01)
*A61K 41/00* (2006.01)
*A61K 47/48* (2006.01)

(56) References Cited

U.S. PATENT DOCUMENTS

| | | | |
|---|---|---|---|
| 5,393,530 A * | 2/1995 | Schneider et al. | 424/450 |
| 5,527,528 A * | 6/1996 | Allen et al. | 424/178.1 |
| 5,773,027 A * | 6/1998 | Bergeron et al. | 424/450 |
| 5,935,942 A * | 8/1999 | Zeimer | 514/63 |
| 6,074,666 A * | 6/2000 | Desai et al. | 424/450 |
| 6,498,945 B1 * | 12/2002 | Alfheim et al. | 600/407 |
| 2002/0006378 A1 * | 1/2002 | Young et al. | 424/1.11 |
| 2005/0152960 A1 * | 7/2005 | Miller et al. | 424/450 |
| 2010/0255080 A1 * | 10/2010 | Sanmiguel et al. | 424/450 |
| 2011/0270056 A1 * | 11/2011 | Jones et al. | 600/317 |
| 2013/0013028 A1 * | 1/2013 | Kriksunov et al. | 607/62 |

* cited by examiner

PEGYLATED COMPOUNDS FOR AGE-RELATED MACULAR DEGENERATION

DOMESTIC PRIORITY UNDER 35 USC 119(e)

This application claims the benefit of U.S. Provisional Application Ser. No. 61/003,653 filed Nov. 19, 2007, entitled "Pegylated Compounds for Age-Related Macular Degeneration" by Volker Albrecht, Stefan Spaniol and Dietrich Scheglmann, which is incorporated by reference herein.

BACKGROUND OF THE INVENTION

1. Field of the Invention

The present invention is related to ophthalmic treatment. Particularly, it relates to photodynamic therapy methods and formulations for treating choroidal neovasculature (CNV) associated with age-related macular degeneration (AMD).

2. Invention Disclosure Statement

Age-related macular degeneration (AMD) is a progressive retinal disease wherein the light-sensing cells in the central area of vision, the macula, stop working and eventually die. The disease is thought to be caused by a combination of genetic and environmental factors, and it is most common in people age sixty and over. AMD is the leading cause of visual impairment in senior citizens. An estimated fifteen million people in the United States have it, and approximately two million new cases are diagnosed annually.

Two basic forms of AMD are exudative neovascular (wet form) and non-neovascular (dry form). Dry form involves macula thinning and pigmentation disturbance. Dry form progresses more slowly compared to wet form. In wet form, abnormal blood vessels known as choroidal neovascularization (CNV) grow under the retina and macula. These new blood vessels bleed and leak fluid causing macula to bulge, thus impairing central vision. Wet form can manifest in two types: classic neovascularization (seen) and occult neovascularization (hidden).

Untreated AMD is a progressive disease state leading to further vision loss. Wet type deteriorates vision faster. Currently, there is no cure for macular degeneration, but some treatments may delay progression or even improve vision. Vision lost due to AMD is generally irreversible.

Current popular AMD treatment methods include laser photocoagulation, Transpupillary Thermo-Therapy (TTT), anti-angiogenic treatment, and most recently PhotoDynamic Therapy (PDT).

Traditionally, thermal lasers were used to cease blood vessel leaking that caused wet form of AMD. Unfortunately, thermal laser treatment also leaves a permanent blind spot in the patient's field of vision. It can also damage normal retinal structure and is suitable only in selected cases where newly formed vessels are not close to the central macular area.

Transpupillary Thermo-Therapy (TTT) utilizes an infrared laser to heat the abnormal blood vessels. This closes the blood vessel without damaging the normal retinal structure. The treatment is aimed at preserving vision. It often requires more than one treatment and regular follow-up appointments for good results.

U.S. Patent Publication 2006/127481 by Kataoka et al., describes the use of polymer micelles for drug delivery to posterior regions of eye affected by neovascularizations. The shell is formed of hydrophilic polymer chains and the core is hydrophobic polymer chains. Such delivery systems are used in PhotoDynamic Therapy (PDT) for treating AMD. A newer PDT treatment option is with verteporfin (Visudyne™ FDA approved) photosensitizer injected into a vein in the patient's arm. After a specific time gap, a non-thermal laser is radiated into the patient's eyes. The radiation activated photosensitizer destroys abnormal blood vessels. Changes in vision, including blurring, decreased sharpness in vision and gaps in vision are commonly reported side effects. This method has limitations because it may require more than one treatment. Moreover, invasive intravenous verteporfin injection unnecessarily exposes the entire body to the photosensitizer.

U.S. Pat. No. 6,942,655 by Peyman, discloses a combination of methods for treating and preventing progression of AMD characterized by fluid leakage. Here, a laser photocoagulation method is used simultaneously or concomitantly with PDT to treat AMD. In another U.S. Pat. No. 6,840,933 by Pang et al, a method is disclosed for detecting and treating growth of feeder blood vessels to neovasculature in choroidal or sub-retinal layers of eye by photocoagulation with laser radiation.

Miller et. al, in U.S. Pat. No. 7,125,542, discloses a method for treating unwanted choroidal neovasculature by combining PDT with an anti-angiogenesis factor, for example, angiostatin or endostatin, or with an apoptosis-modulating factor.

In U.S. Pat. No. 6,800,086 by Strong, use of a PDT method is disclosed with a reduced fluence rate for treating wet form of AMD. The preferred photosensitizer is green porphyrin formulated in liposome for administration. However, these conventional liposome formulations exhibit a short plasma half life and are quickly taken up by mononuclear phagocytes.

U.S. Pat. No. 7,320,786 by Chen discloses a PDT based treatment method for eye diseases. In this method, a photosensitizing agent is tagged to specifically bind to abnormal endothelium cells of neovascular tissue. The preferred photosensitizer absorbs light in the range of 500 to 1100 nm.

The aforementioned prior art treatment methods require multiple treatments and are expensive. Moreover, thermal laser photocoagulation causes damage to normal surrounding retinal cells leaving a permanent blind spot.

In the present invention most of the drawbacks are minimized or eliminated. An improved PDT method and formulation to treat AMD are provided. It improves and stabilizes deteriorating vision and minimizes fluid leakage.

OBJECTIVES AND BRIEF SUMMARY OF THE INVENTION

It is an objective of the present invention, to provide a treatment method and suitably formulated photoactive composition for treating choroids neovasculature (CNV) condition seen in age related macular degeneration.

It is yet another objective of the present invention, to provide a suitable formulation or carrier system, for example pegylation, for administering a required dose of hydrophobic photosensitizer to newly formed choroidal vessels.

It is also another objective of this invention, to confine the drug within the neovasculature region for a longer duration to prevent leakage into the surrounding regions.

It is also the objective of the present invention, to target and occlude the main feeder vessels which supply blood and nutrition to newly formed blood vessels.

Briefly stated, the present invention provides a special photosensitizer formulation and Photodynamic Therapy method for treating choroidal neovascularization (CNV) associated with age-related macular degeneration (AMD). CNV is a major cause for vision loss in elderly patients. A special drug delivery formulation is used to encapsulate the hydrophobic photosensitizer, preferably a pegylated liposome. This improves the solubility and therapeutic index of the photosensitizers. In one preferred embodiment, a pegylated photoactive agent remains confined in the intravascular compartment of neovasculature for a longer duration. Thus efficient elimination of neovascular proliferation and minimal damage to extravascular tissue and normal vessels is ensured. In this method, a hydrophobic photosensitizer that is able to photochemically destroy neovessels is injected into the patient. CNV irradiation with a non-thermal laser follows after a predefined time interval. The excited photosensitizer photocoagulates newly formed blood vessels thereby improving the vision and preventing further loss of vision.

The above and other objects, features and advantages of the present invention will become apparent from the following description read in conjunction with the accompanying drawings.

DETAILED DESCRIPTION OF PREFERRED EMBODIMENTS

Figure 1:
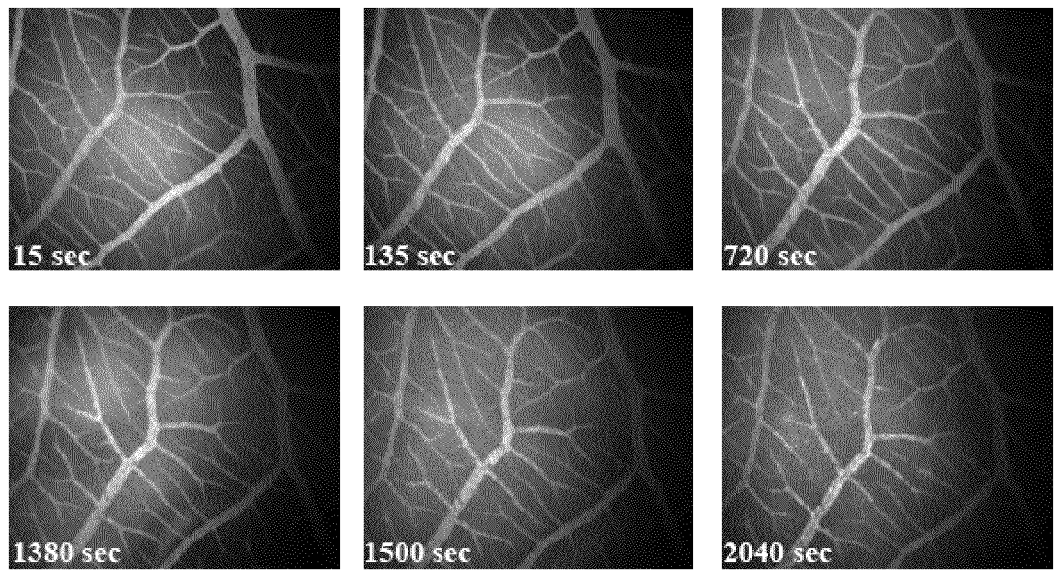
FIG. 1—Fluorescence angiographies obtained after injecting pegylated liposome loaded with m-THPC (0.5 or 1 mg/kg body weight) within blood vessels and the surrounding tissue at different time after i.v. injection.

PhotoDynamic Therapy (PDT) is a new treatment modality for treating hyperproliferative tissue and hyper-vascularization. It is an approved treatment for choroidal neovascularization (CNV) associated with age-related macular degeneration (AMD), a leading cause of visual disability in elderly people. Here, the central portion of the retina—the macula—deteriorates, and central vision is lost. Central vision is required for reading, driving, watching television, recognizing people and performing many other activities of daily living. Peripheral vision generally remains intact.

PDT generally involves administration of a hydrophobic photosensitizer selected from the group of dihydro- and tetrahydro porphyrins followed by irradiation of the site with laser energy of an appropriate wavelength, which occurs after a predefined time interval known as the Dose-Light-Interval (DLI). The photoactivated photosensitizing agent generates singlet oxygen to induce a cytotoxic effect in the treatment zone.

General Treatment Procedure

Pegylated mTHPC is administered to the patient and the retina is illuminated with a mercury-arc lamp. Time dependent fluorescence angiography, were used to determine the extravasation kinetics of the photosensitizer. Aberrant choroidal neovasculature and its associated feeder vessels are identified and a therapeutic dose of photosensitizer is administered to the patient to perform PDT. The photosensitizer exposed vessels are irradiated sufficiently to inhibit blood flow by sealing the vessels permanently.

In the present invention, a photodynamic method and a specially formulated composition are used to effectively treat CNV, in order to improve and preserve vision. The photosensitizing agent is administrated to the patient systemically. Drug delivery systems, such as liposomes, microspheres, nanospheres or pegylation methods, are used for improving the therapeutic index of encapsulated drugs. The term photosensitizer, as used herein, further includes photosensitizer derivatives, and their natural precursors, such as Amino-Levulinic Acid (ALA) for protoporphyrin IX.

In a preferred embodiment of present invention, a pegylated liposomal formulation of hydrophobic photosensitizers is used for treating CNV. The hydrophobic nature of the drug ensures rapid cellular uptake and localization at critical intracellular membranous organelles. Hydrophobic photosensitizers have increased affinity for low density lipoprotein (LDL). Malignant cell and neovascular endothelial cells show increased expression of LDL receptors. Thus the hydrophobic photosensitizer can easily traverse the lipid membrane of these cells. Hydrophobic photosensitizers, however, have poor solubility in physiological acceptable media. Drug delivery systems are presented, here, which can improve their solubility without damaging their benefits and activity.

A photosensitizer entrapped within pegylated liposome improves plasma half-life of the drug. In one embodiment, a hydrophobic photosensitizer is directly pegylated without being encapsulated into a liposome vesicle. A pegylated photosensitizer is protected from immune system enzymatic and cellular degradation. After a predetermined time interval, the CNV region is irradiated with a non-thermal laser for a specific time and energy without damaging the healthy retinal cells in the regions.

The present invention is further illustrated by the following examples, but is not limited thereby.

Example 1

Pegylated liposomes loaded with hydrophobic photosensitizer, meso-tetra (hydroxyphenyl) chlorin (m-THPC or Temoporfin) are used to photodynamically close neovascular vessels. The m-THPC loaded pegylated liposomes are intravenously injected into the patient. After a predefined time interval, (dose-light-interval DLI) irradiation of CNV with a non-thermal laser follows. The pegylated liposome loaded with m-THPC minimizes extravasation, and maximizes photothrombic activity. Moreover, use of pegylated photosensitizer is safer as it remains confined within intravascular compartment as compared to the current art, such as Verteporfin, which is often found to leak over time, causing damage to surrounding normal retinal tissue upon irradiation of the eye.

Example 2

Preparation of Pegylated Liposome Loaded with m-THPC Solution

The pegylated liposomal bilayer loaded with m-THPC based on dipalmitoyl-phosphatidyl choline (DPPC) is used. Stock solution (1.5 mg m-THPC/ml) 3 ml vial is diluted in 5% sterile glucose for further dilution.

Pegylated Liposome Entrapping m-THPC Basically Comprises of:
  m-THPC
  dipalmitoyl-phosphatidyl choline (DPPC)
  dipalmitoyl-phosphatidyl glycerol (DPPG)
  pegylated disteareoryl-phosphatidyl ethanolamine (DSPE)

A preferred ratio of the synthetic phospholipids for phosphatidyl choline to phosphatidyl glycerol is to pegylated disteareoryl-phosphatidyl ethanolamine about 9:1:1. Disteareoryl-phosphatidyl ethanolamine (DSPE) is pegylated using methoxyl polyethylene gycol (MPEG) polymer.

A drug dosage range from 0.25 to 1.0 mg/kg of body weight is used to evaluate extravasation kinetics of photosensitizer and PDT effect using chick chorioallantoic membrane (CAM) as in vivo vascular model.

Pharmacokinetic and PDT Studies Using Chick Chorioallantoic Membrane (CAM)

Figure 2:
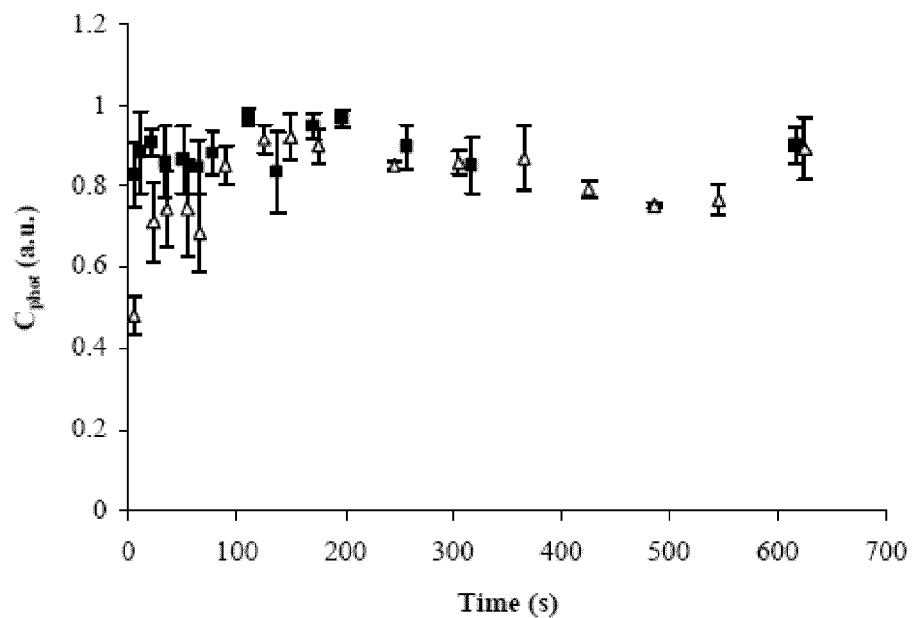
FIG. 2—The fluorescence pharmacokinetic profile measured after injecting pegylated liposome loaded with m-THPC at doses of 0.5 (■) or 1 (Δ) mg/kg body weight. Each data point is the mean of five values obtained with 5 different eggs and calculated after normalization (Mean±SD, n=5)

Disinfected fertilized chicken eggs were kept in a hatching incubator equipped with an automatic rotator and set at 37° C. and 60% humidity. The egg shells of fertilized chicken eggs were opened on embryo development day 13 (body weight ~10 g, blood volume ~1 ml), and five embryos were injected for each drug dosage. Following an intravenous injection of pegylated liposome loaded with m-THPC (0.5 or 1 mg/kg of body weight), time dependent fluorescence angiographies were carried out to determine the extravasation kinetics of the photosensitizer. Fluorescence imaging was performed using a mercury-arc lamp. The fluorescence angiographies obtained at different time intervals are shown in FIG. 1. FIG. 1 shows the blood vessels and the surrounding tissue at different times after intravenous injection. The dye remains within the blood stream over the entire observable time (up to 2040 sec). The calculation of normalized photographic contrast $C_{phot}$ from the above fluorescence image at different times following drug injection evaluates the extent of drug leakage. FIG. 2 graphically demonstrates time dependent evolution of $C_{phot}$ for pegylated liposome loaded with m-THPC (0.5 or 1 mg/kg of body weight). FIG. 2 demonstrates that irrespective of the drug concentration, pegylated liposome loaded with m-THPC remains in the intravascular compartment up to 600 sec, a small amount is found to leak out after 650 sec from the blood vessel. Thus based on FIG. 1 some drug will be present in the blood vessel well beyond 650 seconds after administration, but FIG. 2 demonstrates that before 600 seconds the drug will exist exclusively within the intravascular compartment.

Photo-Toxicity Assays:

PDT assay was performed 30 seconds after injecting pegylated liposome loaded with m-THPC. Drug dosage ranging from 0.25 to 1 mg/kg of body weight with different light doses (12.5 to 100 J/cm$^2$, excitation wavelength=400-440 nm) were used. Vascular damage caused by phototoxicity was assessed using fluorescence angiography, performed by injecting 10 μl of sulforhodamine101 ($\lambda_{ex}$=500-550 nm, $\lambda_{em}$=>610 nm) 24 hours after PDT treatment.

Results

Figure 3:
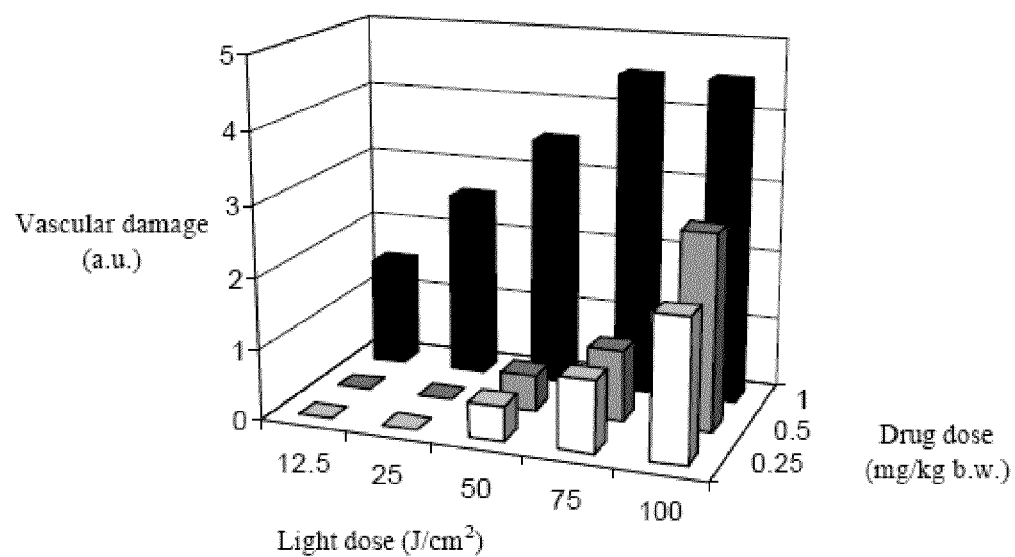
FIG. 3—Vascular damage of the chick chorioallantoic membrane (CAM) blood vessels evaluated 24 hours after PDT for different light and drug doses.
Figure 4:
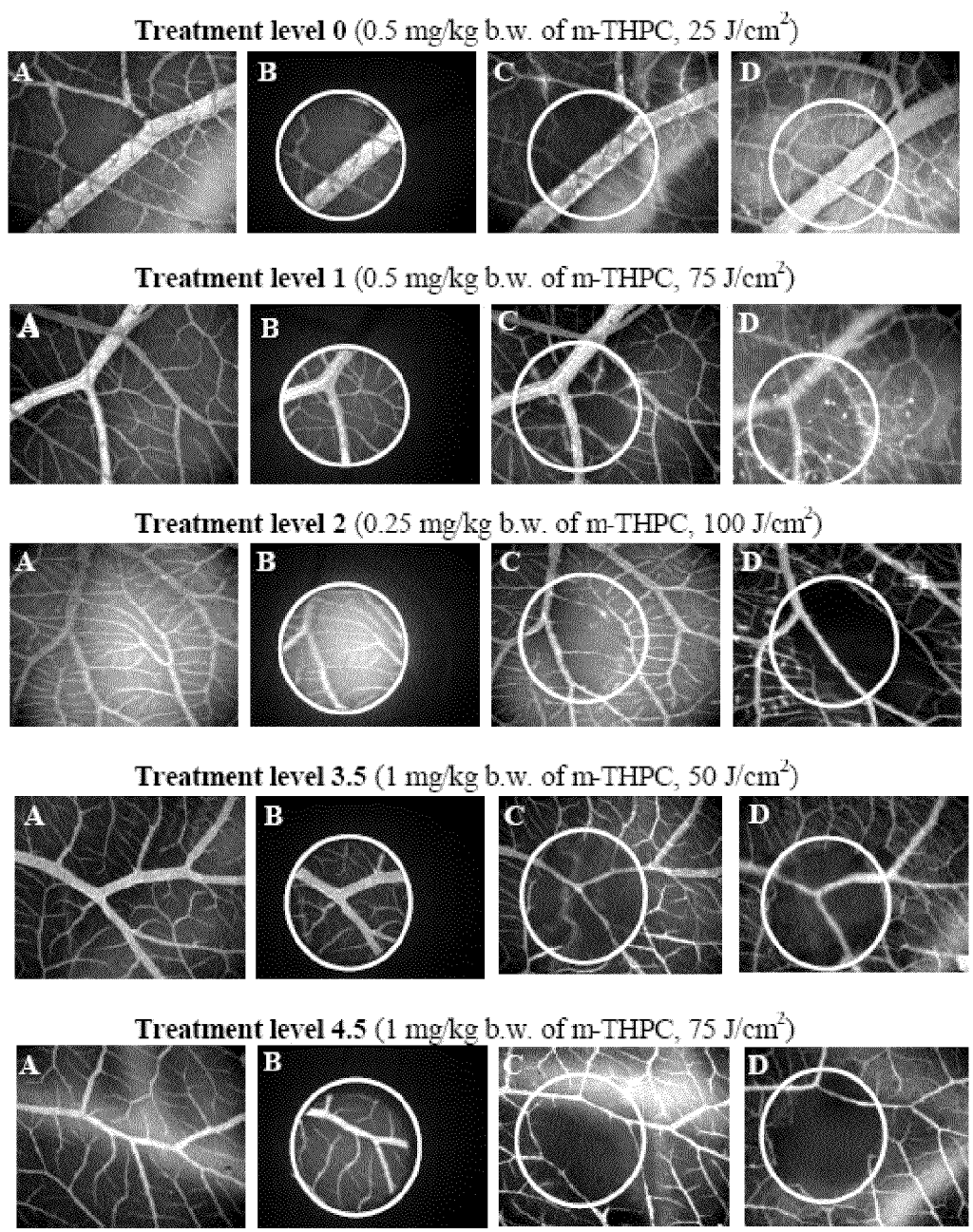
FIG. 4—Treatment results are illustrated after PDT with pegylated liposome loaded with m-THPC on CAM blood vessels.

FIGS. 3 and 4 illustrate the results. From these figures, it can be seen that when the drug dosage and light doses are smaller than 0.5 mg/kg of body weight and 25 J/cm$^2$, respectively, no visible vascular damage was observed. It can be noted that the photothrombic efficiency was increased with applied light doses. However, an increase in drug dosage from 0.25 to 0.5 mg/kg of body weight led to no significant difference in vascular damage when the irradiation was performed at light doses below 100 J/cm$^2$. FIG. 3 demonstrates that optimal treatment result is observed with drug dosage range of 0.25 and 0.5 mg/kg of body weight, and a light dose of 100 J/cm$^2$. In FIG. 4, treatment results are illustrated after PDT with pegylated liposome loaded with m-THPC on CAM blood vessels. Irradiation was performed with light doses ranging from 12.5 to 100 J/cm$^2$. (A) Fluorescence angiography of pegylated liposome loaded with m-THPC ($\lambda_{ex}$=420±20 nm; $\lambda_{em}$>610 nm) performed before PDT (#0 sec after dye injection). (B) Fluorescence angiography of pegylated liposome loaded with m-THPC during irradiation. The diameter of the irradiation area (white circle) was 2 mm. (C) Fluorescence angiography of pegylated liposome loaded with m-THPC immediately after PDT. (D) Fluorescence angiography of sulforhodamine 101 ($\lambda_{ex}$=500-550 nm; $\lambda_{em}$>610 nm) 24 hours after PDT.

Similar vascular damage is observed with high drug dosage (1 mg/kg of body weight) and low light doses (25 and 50 J/cm$^2$) see FIG. 4(D). However, irradiation with light doses higher than 75 J/cm$^2$ after injecting high drug dosage, can often lead to unwanted occlusion of larger blood vessel leading to closure of retinal vessels and impairment of patient's visual acuity. Hence, low drug dosage and light dose were ineffective to cause any vascular closure while high drug dosage and light dose induced unwanted damage to large blood vessels in retina. Therefore, to avoid damage to other major vessels and retinal cells, high drug dosage and high light dose need to be avoided. Effective photothrombic efficiency can be achieved by increasing applied light dose with low drug dosage level or by increasing the drug dosage and lower the light lose.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A chemical formulation for the delivery of a hydrophobic drug to a choroidal neovascular region, comprising:
   a carrier for solubilizing a hydrophobic drug; and
   a therapeutically effective amount of hydrophobic photosensitize; wherein said carrier is a liposomal bilayer comprising synthetic phospholipids that are a mixture of dipalmitoyl phosphatidyl choline (DPPC), dipalmitoyl phosphatidyl glycerol (DPPG), and pegylated distearoyl phosphatidyl ethanol amine (PEG-DSPE) present in a weight ratio of DPPC:DPPG:PEG-DSPE of 9:1:1 and said drug is present in said liposomal bilayer; and wherein said hydrophobic photosensitizer is temoporfin.

2. A method for effecting closure of choroidal neovasculature related to age related macular degeneration (AMD) in patients using photodynamic therapy (PDT) comprising the steps of:
   administering a therapeutically effective amount of pegylated liposome comprising synthetic phospholipids that are a mixture of dipalmitoyl phosphatidyl choline (DPPC), dipalmitoyl phosphatidyl glycerol (DPPG), and pegylated distearoyl phosphatidyl ethanol amine (PEG-DSPE) present in a weight ratio of DPPC:DPPG:PEG-DSPE of 9:1:1 and, which has a predetermined amount of a hydrophobic photosensitizer in its bilayer;
   allowing sufficient time to release and localize said photosensitizer in chorodial neovasculature; and
   irradiating the photosensitizer with non-thermal laser radiation, so as to occlude the choroidal neovasculature; and wherein said photosensitizer is temoporfin administered at a drug dosage ranging between about 0.25 to 1.0 mg/kg body weight.

3. The method according to claim 2, wherein said photosensitizer is administered intravenously.

4. The method according to claim 2, wherein said photosensitizer remains confined within the choroidal neovasculature for at least 700 sec.

5. The method according to claim 2, wherein said non-thermal laser irradiation is applied at a power density between about 12.5 J/cm² to 100 J/cm².

\* \* \* \* \*